United States Patent
Tsuchiya

[11] Patent Number: 5,913,410
[45] Date of Patent: Jun. 22, 1999

[54] ORTHOPEDIC BELT FOR PELVIS

[75] Inventor: Yoshihiro Tsuchiya, Kyoto, Japan

[73] Assignee: You Co., Ltd., Kyoto, Japan

[21] Appl. No.: 09/028,573

[22] Filed: Feb. 24, 1998

[30] Foreign Application Priority Data

Aug. 26, 1997 [JP] Japan ................................. 9-246212

[51] Int. Cl.$^6$ ................................................. A61F 5/02
[52] U.S. Cl. ........................... 2/311; 2/92; 2/44; 602/19; 602/60; 128/99.1
[58] Field of Search ............................... 2/311, 312, 44, 2/92, 338, 318, 321, 455, 456; 602/19, 60, 61; 128/99.1, 100.1, 101.1

[56] References Cited

U.S. PATENT DOCUMENTS

| | | | |
|---|---|---|---|
| 3,393,675 | 7/1968 | Trznadel et al. | 128/101.1 |
| 4,833,730 | 5/1989 | Nelson | 2/44 |
| 5,083,554 | 1/1992 | Toso | 128/101.1 X |
| 5,122,111 | 6/1992 | Sebastian et al. | 602/19 |
| 5,147,261 | 9/1992 | Smith et al. | 602/19 X |
| 5,207,635 | 5/1993 | Richards et al. | 602/19 |
| 5,310,401 | 5/1994 | Striano | 602/19 |
| 5,445,601 | 8/1995 | Harlow | 602/19 |
| 5,551,085 | 9/1996 | Leighton | 602/19 |
| 5,656,021 | 8/1997 | Greengarg | 602/19 |
| 5,690,122 | 11/1997 | Weber-Unger | 602/19 X |

*Primary Examiner*—Gloria Hale
*Attorney, Agent, or Firm*—Bacon & Thomas

[57] ABSTRACT

An orthopedic belt for pelvis is disclosed, which comprises an upper belt made of an elastic cloth which covers mainly a sacroiliac joint and a lower belt made of the same elastic cloth which covers mainly a hip joint, wherein the right and left end portions of both upper and lower belts are joined to each other in an overlapped state to form both end portions of the orthopedic belt; middle portions in the length of the upper and lower belts are connected to each other in a parallel state via a plurality of cloth-made connecting pieces; a pocket is provided inside a central portion in the length of the upper belt; an orthopedic block for sacral bone support having a ceramic portion is received in the pocket; and hook and eye members for connecting the both end portions of the orthopedic belt upon being interlocked to each other are provided in both end portions of the orthopedic belt. By the use of the orthopedic belt for pelvis according to the present invention, various chronic diseases of human bodies caused by misalignment of the pelvis, including lumbago, are prevented or treated since the inclination of the pelvis caused by weakening of the orthostatic muscle can be corrected (remedied).

1 Claim, 2 Drawing Sheets

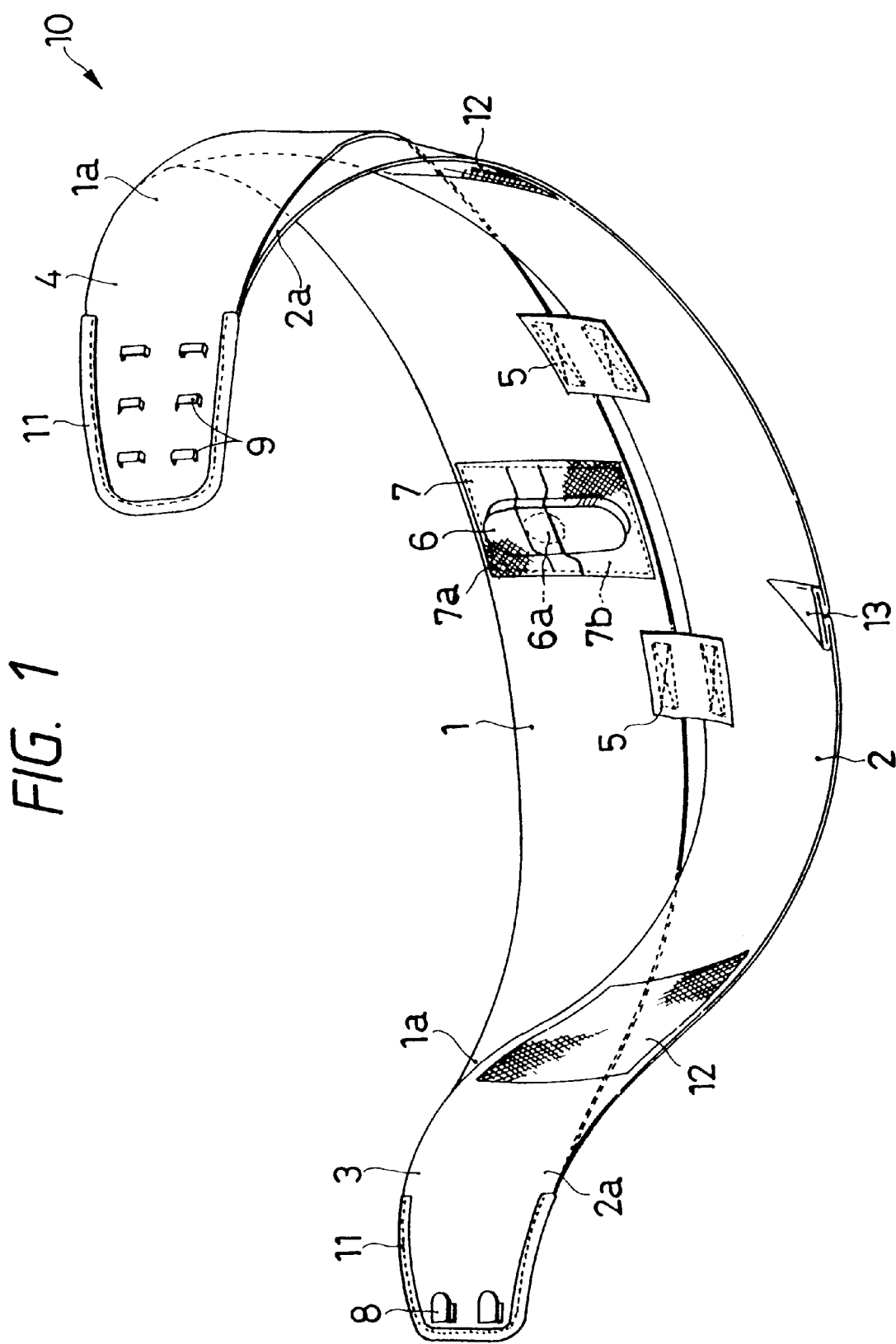

ORTHOPEDIC BELT FOR PELVIS

FIELD OF THE INVENTION

The present invention relates to an orthopedic belt for a pelvis.

BACKGROUND OF THE INVENTION

In recent years, with the advance of civilization, people no longer have time for considerable walking. Consequently, it is difficult to maintain a healthy standing posture due to weakened orthostatic muscle (a general name of a group of muscles functioning for maintaining the standing posture, such as musculus gluteus maximus, musculus gluteus medius, musculus iliopsoas, and back muscles).

For this reason, in most people, the pelvis (which is a junction between two legs supporting the whole weight and the upper half of the body) has become inclined. If the pelvis is inclined, the backbone which is positioned above the pelvis, comprising 24 vertebrae, is also inclined.

If the backbone is inclined, in order to keep balance, the skeleton from the neck to the legs with the backbone being the center, forms a delicate curve. Nerves of the whole body and accompanying blood capillaries (cerebrospinal nervous system) extend from the spinal cord.

Orthopedic belts or corsets for pelvis, having various structures have hitherto been known, however none of them are fully able to exhibit an orthopedic action for pelvis.

If the above-described distortion (a bad posture) of the skeleton (mainly the pelvis and backbone) becomes chronic, various branch organs (i.e. spinal nerves) are compressed by the distortion of the backbone, thus causing a chronic condition.

SUMMARY OF THE INVENTION

An objective of the present invention is to provide an orthopedic belt for the pelvis for correcting the inclination of a pelvis caused by weakening of the orthostatic muscles. The belt of this invention can be used to treat such chronic conditions, including lumbago, caused by the above noted spinal distortion.

For the purpose of achieving the above-described objective, the orthopedic belt for pelvis according to the present invention comprises an upper belt made of an elastic cloth for covering mainly the sacroiliac joint and a lower belt made of the same elastic cloth for covering mainly a hip joint. The right and left end portions of both the upper and the lower belts are joined to each other in an overlapped state to form both end portions of the orthopedic belt. Middle portions in the length of the upper and lower belts are connected to each other in a parallel state via a plurality of cloth connecting pieces. A pocket portion is provided inside a central portion in the length of the upper belt for holding an orthopedic block for the sacral bone. The orthopedic block includes a ceramic member as a portion thereof. Hook and eye members for connecting the both end portions of the orthopedic belt upon being interlocked to each other are provided in the both end portions of the orthopedic belt.

The ceramic may be, for example, an infrared light-releasing ceramic, or the like.

BRIEF DESCRIPTION OF THE DRAWINGS

FIG. 1 is a schematic perspective view of the orthopedic belt for pelvis according to the present invention.

FIG. 2 shows the order of applying the orthopedic belt for pelvis according to the present invention, in which

DETAILED DESCRIPTION OF PREFERRED EMBODIMENT

Figure 2A:
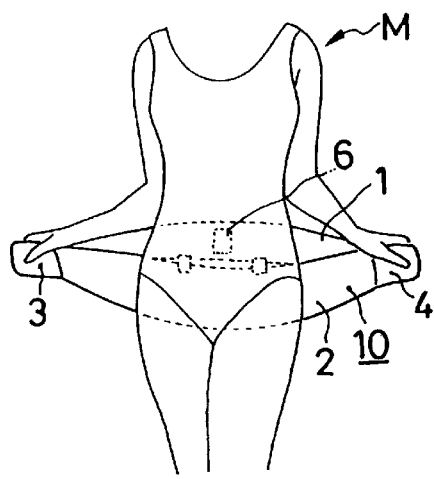
FIG. 2(a) is a schematic perspective view of the orthopedic belt for pelvis according to the present invention being applied on the hip before wearing.
Figure 2B:
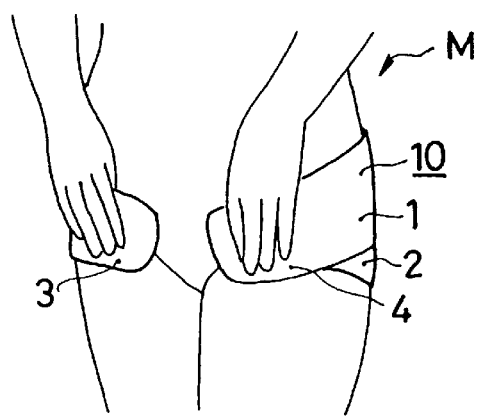
FIG. 2(b) is a schematic perspective view of the orthopedic belt for pelvis where both end portions thereof are overlapped in a non-stretched state in front of the body.

The embodiment of the present invention will be described with reference to the accompanying drawings.

First of all, with reference to FIG. 1, an orthopedic belt 10 for pelvis according to the present invention is provided with an upper belt 1 made of an elastic cloth for covering mainly a sacroiliac joint 23 and a lower belt 2 made of the same elastic cloth for covering mainly a hip joint 24. Right and left end portions 1a, 1a and 2a, 2a of the both upper and lower belts 1, 2 are joined to each other in an overlapped state to form both end portions 3, 4 of the orthopedic belt.

That is, the two specific belts 1, 2 (belts having such knitted structure that they hardly block the blood circulation even upon application of a pressure) are integrally joined to each other by sewing in the right and left end portions 1a, 1a and 2a, 2a. As hook and eye members for connecting the both right and left end portions 3, 4 of the orthopedic belt to each other, male hook 8 are provided inside the left end portion 3 (the side of the human body), and female eye members 9 are provided outside the right end portion 4 (the surface side opposite to the human body), respectively. Also, strip-like edging cloths 11, 11 are provided in the both right and left end portions 3, 4 of the orthopedic belt joined to each other by sewing.

Middle portions in the length of the upper and lower belts 1, 2 are in a parallel state, and particularly, in the vicinity of the central portions thereof, a plural number of cloth-made connecting pieces 5, 5 are placed over them, whereby the upper and lower belts 1, 2 are connected to each other via these connecting pieces 5, 5.

Also, a pocket portion 7 is provided inside a central portion in the length of the upper belt 1, and an orthopedic block 6 for sacral bone (supporter for sacral bone) having a ceramic portion 6a comprising, for example, an infrared light-releasing ceramic, is received in the pocket portion 7.

It is preferable to use, for example, a hard polyurethane resin foam as the orthopedic block 6 for supporting the sacral bone.

Furthermore, in this embodiment, the pocket portion 7 comprises an upper cloth 7a and a lower cloth 7b; a lower end portion of the upper cloth 7a is partly overlapped with an upper end portion of the lower cloth 7b; and an upper edge of the upper cloth 7a is sewn with right and left side edges of the upper cloth 7a in a reverse U-shape, and a lower edge of the lower cloth 7b is sewn with right and left side edges of the lower cloth 7b in a U-shape, respectively, in each of which is provided with an opening. Thus, the orthopedic block 6 for supporting the sacral bone can be freely removed. Also, cloth for preventing pressure, i.e., cloths 12, 12 are respectively provided by sewing in bent portions of the belt toward the both end portions 3, 4 of the orthopedic belt in which the right and left end portions 1a, 1a and 2a, 2a of both of the upper and lower belts 1, 2 are joined to each other in an overlapped state.

Also, a center dart 13 is provided in a central lower edge portion of the lower belt 2 such that when fitting, the belt readily follows the figure of a body.

In order to correct the inclined pelvis to the correct position, it is necessary to provide support for replacing the muscle in order to support the pelvis at the right position. The orthopedic belt for pelvis according to the present invention is very suitable for providing such support for orthopedics of the pelvis.

In general, the properties of the inclined pelvis are as follows.

Since it is difficult for an orthostatic muscle to support the body weight, a person will typically stand while applying the body weight to either one of the right and left legs (in a state of relying on bone power rather than muscle power). Thus, there is caused an unevenness between the right and left iliac bones 21, 21 in a pelvis 20 (see FIG. 2(e)). Also, the right and left iliac bones 21, 21 are as a whole in improper alignment. This produces shears between sacroiliac joints 23, 23 (see FIG. 2(e)) as well as between symphysial portions of pubes (not illustrated). Accordingly, if the pelvis 20 is improperly aligned, then the backbone comprising 24 vertebrae including lumbar vertebrae 25 will also be improperly aligned.

In order to recover the original right position from such state, the orthopedic belt 10 for pelvis according to the present invention is used.

The method for use of the orthopedic belt 10 for pelvis according to the present invention will now be explained by referring to FIG. 2.

First of all, the orthopedic belt 10 for pelvis according to the present invention is placed along a hip from the rear of a human body M (see FIG. 2(a)) and then wrapped around the body without applying a force. At this time, both end portions 3, 4 of the orthopedic belt 10 for pelvis are applied with one end portion facing the other in a non-stretched state in front of the human body M (see FIG. 2(b)) and preferably with a gap of about 12 cm from each other therebetween.

Figure 2C:
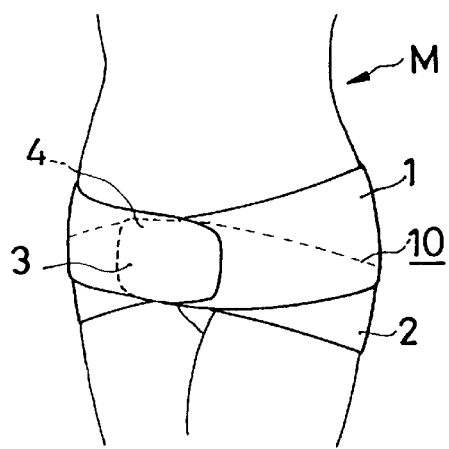
FIG. 2(c) is a schematic perspective view of the orthopedic belt for pelvis, when worn, where the both end portions thereof are overlapped in a stretched state and connected to each other.

Next, the orthopedic belt 10 for pelvis is stretched, both end portions 3, 4 thereof are overlapped, and the male and female hook and eye members 8, 9 are interlocked to thereby connect both end portions 3, 4 of the belt to each other, whereby the orthopedic belt 10 for pelvis is thus worn (see FIG. 2(c)).

At this time, the lower belt 2 is strongly stretched right and left such that a one-third of the lower belt 2 engages a leg side from a boundary between the hip and the leg and then put in front of the human body M, followed by completion of the interlocking. In front of the human body M, the belt is stopped at a position with a proper strength, and both end portions 3, 4 of the belt as stopped are set on the pubes. Thus, the hip joints 24, 24 are covered by the lower belt 2.

Figure 2D:
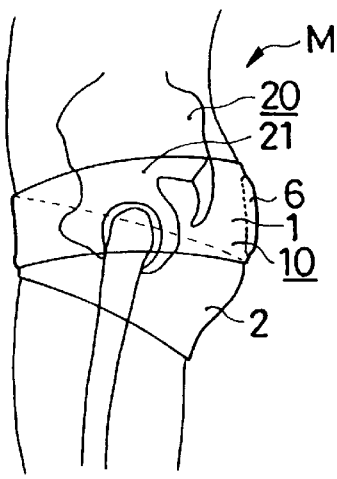
FIG. 2(d) is a schematic side view thereof when worn.
Figure 2E:
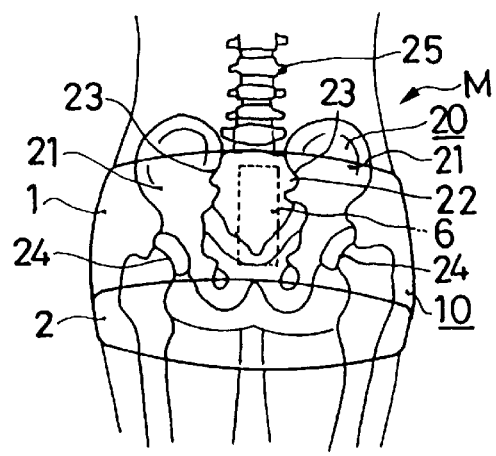
FIG. 2(e) is a schematic back view thereof when worn where the pelvis is illustrated.

Also, the ceramic portion 6a of the orthopedic block 6 which is located inside the central portion of the upper belt 1, is positioned just on a rear side of a sacral bone 22, i.e., just under the backbone (see FIG. 2(d) and FIG. 2(e)).

The function of the ceramic 6a is to convert waves which are harmful for humans, such as ultraviolet rays or electromagnetic waves, into non-harmful waves. This is accomplished by using an infrared light-releasing ceramic.

According to the orthopedic belt 10 for pelvis of this invention, the upper belt 1 not only pushes both iliac bones 21, 21 up from the rear side to the front side but also supports the sacral bone 22. Also, the upper belt 1 adjusts the shears between sacroiliac joints 23, 23 as well as between symphysial portions of pubes (not illustrated). On the other hand, the lower belt 2 pushes the hip joints (greater trochanters) 24,24 as a point of contact between two legs (femurs) and the pelvis 20 to which the whole body weight is applied up from the rear side to the front side.

In this connection, considerable support is applied to the surrounding of the pubis in the front side in which the both end portions 3, 4 of the both upper and lower belts 1, 2 are integrally joined to each other. This promotes an effect for massage (finger-pressure) to meridian points in the area of the pubis.

Also, since the cloth for preventing pressure, i.e., cloths 12, 12 are respectively provided in the bent portions of the belt toward the both end portions 3, 4 of the orthopedic belt 10 for pelvis, there is an advantage that no pain is caused by a compression based on the pressure of the two belts 1, 2 even for persons of sedentary habits.

In addition, since the orthopedic block 6 for sacral bone (supporter for sacral bone) having a ceramic portion 6a can be freely removed, there is an advantage that for example, for those who feel a sense of incongruity when they are in bed, if the orthopedic block 6 is obstructive, it can be readily removed.

As described above, the orthopedic belt for pelvis according to the present invention comprises an upper belt made of an elastic cloth which covers mainly a sacroiliac joint and a lower belt made of the same elastic cloth which covers mainly a sacroiliac joint and a lower belt made of the same elastic cloth which covers mainly a hip joint, wherein the right and left end portions of both the upper and lower belts are joined to each other in an overlapped state to form both end portions of the orthopedic belt; middle portions in the length of the upper and lower belts are connected to each other in a parallel state via a plurality cloth-made connecting pieces; a pocket is provided inside a central portion in the length of the upper belt; an orthopedic block for sacral bone support having a ceramic portion is received in the pocket; and hook and eye members for connecting the both end portions of the orthopedic belt upon being interlocked to each other are provided in both end portions of the orthopedic belt. In order to correct the misalignment of the pelvis, the present invention is very suitable for adding support for replacing the muscle in order to support the pelvis at the right position. Also, by the use of the orthopedic belt for pelvis according to the present invention, the misalignment of the pelvis caused by weakening of the orthostatic muscle can be corrected (remedied), leading to such an effect that various chronic diseases including lumbago can be prevented or treated.

While the invention has been described in detail and with reference to specific embodiments thereof, it will be apparent to one skilled in the art that various changes and modifications can be made therein without departing from the spirit and scope thereof.

What is claimed is:

1. An orthopedic belt for supporting a pelvis which comprises:

an upper belt made of an elastic cloth for covering mainly a sacroiliac joint and a lower belt made of the same elastic cloth for covering mainly a hip joint, said upper and lower belts having left and right end portions wherein the right and left end portions of said upper and lower belts are joined to each other in an overlapped state to thereby define end portions of said orthopedic belt;

each of said upper and lower belts having a middle portion between said end portions, said middle portion of said upper and lower belts being parallel connected to each other by a plurality of cloth connecting pieces;

said upper belt including a pocket portion inside a central portion thereof;

an orthopedic block for supporting a sacral bone, said orthopedic block being located in said pocket portion and said block including a piece of ceramic;

said end portions of said orthopedic belt including hook and eye members for connecting said end portions of the orthopedic belt to each other by interlocking of said hook and eye members.

* * * * *